United States Patent

Valkovich et al.

[11] 4,388,200
[45] Jun. 14, 1983

[54] QUATERNARY AMMONIUM SALT COMPOSITION AND LUBRICATING OIL CONTAINING SAME

[75] Inventors: Phillip B. Valkovich, Spring, Tex.; Kenneth G. Hammond, Poughkeepsie, N.Y.

[73] Assignee: Texaco Inc., White Plains, N.Y.

[21] Appl. No.: 353,306

[22] Filed: Mar. 1, 1982

[51] Int. Cl.$^3$ ............................................. C10M 1/32
[52] U.S. Cl. ................................ 252/34; 252/51.5 A; 546/281
[58] Field of Search ........................... 252/34, 51.5 A; 546/281

[56] References Cited

U.S. PATENT DOCUMENTS

| 4,108,858 | 8/1978 | Malec | 252/34 |
| 4,326,973 | 4/1982 | Hammond et al. | 252/34 |
| 4,338,206 | 7/1982 | Hammond et al. | 252/34 |
| 4,339,336 | 7/1982 | Hammond et al. | 252/34 |

Primary Examiner—Jacqueline V. Howard
Attorney, Agent, or Firm—Carl G. Ries; Robert A. Kulason; James J. O'Loughlin

[57] ABSTRACT

A quaternary ammonium salt composition represented by the formula:

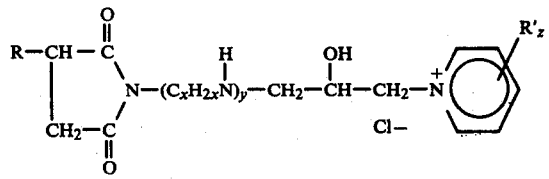

in which R is a hydrocarbyl radical having from 25 to 200 carbon atoms, x is a number from 2 to 4, y has a value from 0 to 4, R' is a hydrocarbyl radical having from 1 to 10 carbon atoms, and z is a number from 0 to 2, is provided, as well as a method of preparation and a lubricating oil composition containing same.

10 Claims, No Drawings

QUATERNARY AMMONIUM SALT COMPOSITION AND LUBRICATING OIL CONTAINING SAME

BACKGROUND OF THE INVENTION

1. Field of the Invention

Internal combustion engines operate under a wide range of temperatures including low-temperature stop-and-go service as well as high-temperature conditions produced by continuous high speed driving. Stop-and-go driving, particularly during cold, damp weather conditions, leads to the formation of sludge in the crankcase and in the oil passages of a gasoline engine. This sludge seriously limits the ability of the crankcase oil to lubricate the bearings and sliding wear surfaces in the engine or to act as a coolant. In addition, the sludge serves to contribute to rust formation within the engine because it tends to retain water in areas susceptible to corrosion. The noted problems are compounded by lubrication service maintenance recommendations calling for extended oil drain intervals.

It is known to employ nitrogen-containing dispersants and/or detergents in the formulation of crankcase lubricating oil compositions. Many of the known dispersant/detergent compounds are based on the reaction of an alkenylsuccinic acid or anhydride with an amine or polyamine to produce an alkenylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a dispersant reaction product typically containing from about 0.5 to 5% nitrogen. These dispersant additives exhibited a high degree of oil solubility and have been found to be effective for dispersing the sludge that is formed under severe low temperature stop-and-go engine operating conditions. However, it has become increasingly difficult to formulate lubricants with these additives which meet the present requirements with respect to the prevention or inhibition of the formation of varnish.

2. Description of the Prior Art

A copending application, Ser. No. 224,728, filed on Jan. 13, 1981, discloses a quaternary ammonium succinimide salt composition formed from an N-(haloalkyl)hydrocarbylsuccinimide and a heteroaromatic amine and lubricants containing same.

A copending application, Ser. No. 246,512, filed on Mar. 21, 1981, discloses a quaternary ammonium succinimide salt composition prepared from an aminopyridine derived hydrocarbyl succinimide and an alkyl halide and lubricants containing same.

SUMMARY OF THE INVENTION

The quaternary ammonium salt composition of this invention is represented by the formula:

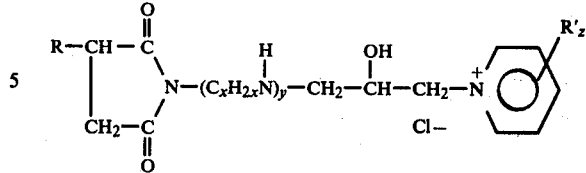

in which R is a hydrocarbyl radical having from 25 to 200 carbon atoms, X is a number from 2 to 4, y has a value from 0 to 4, R is a hydrocarbyl radical having from 1 to 10 carbon atoms and z is a number from 0 to 2.

The novel quaternary ammonium salt composition of the invention is prepared by reacting a hydrocarbon-substituted succinic anhydride with a polyamine to produce an intermediate hydrocarbon derivative of a succinic compound. This intermediate is then reacted with epichlorohydrin and a tertiary heteroaromatic amine to form the prescribed quaternary ammonium salt dispersant of the invention.

The lubricating oil composition or lubricant concentrate of the invention comprises a substrate of lubricant viscosity and an effective dispersant amount of the prescribed quaternary ammonium salt of the invention.

DESCRIPTION OF THE PREFERRED INVENTION

The novel quaternary ammonium salt composition of the invention is represented by the formula:

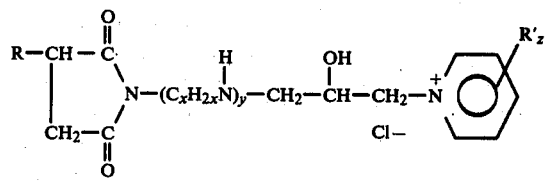

in which R is a hydrocarbyl radical having from 25 to 200 carbon atoms, x is a number from 2 to 4, y has a value from 0 to 4, R' is a hydrocarbyl radical having from 1 to 10 carbon atoms and z is a number from 0 to 2.

A preferred additive of the invention is a quaternary ammonium succinimide salt in which R is an alkenyl radical, such as a polybutenyl, polyisobutenyl, and polypropenyl radical, having from 50 to 125 carbon atoms or still more preferred from 70 to 100 carbon atoms.

The preparation of a quaternary ammonium succinimide salt composition of the invention begins with a hydrocarbyl-substituted succinimide intermediate. This starting succinimide reactant is represented by the formula:

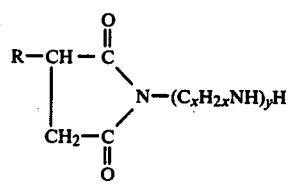

in which R, x and y have values noted above. The method for preparing hydrocarbyl succinimides is well known in the art and does not constitute a part of this invention.

The hydrocarbyl succinimide is reacted with epichlorohydrin and a tertiary heteroaromatic amine in order to form the prescribed quaternary ammonium salt. The effective tertiary heteroaromatic amine is represented by the formula:

in which R' is a hydrocarbyl radical having from 1 to 10 carbon atoms and z is a number from 0 to 2.

The preferred heteroaromatic amine is one in which R' is a lower aliphatic hydrocarbon radical having from 1 to 4 carbon atoms and z is 1.

Examples of effective tertiary heteroaromatic amines include pyridine, 3-methylpyridine, 3,4-dimethylpyridine, 4-methylpyridine, 3-ethylpyridine, and 4-ethylpyridine.

The following examples illustrate the method for preparing the quaternary ammonium salt compositon of the invention.

EXAMPLE I

Fourteen hundred grams of polyisobutenyl (1300 MW) succinic acid anhydride (saponification number of 51) was mixed with 180 grams of ethylenediamine (approximately a 1:5 mole ratio) in a reaction vessel under an inert nitrogen blanket. The mixture was heated at 90° C. for 3 hours and then stripped under a vacuum until no further distillate evolved from the intermediate reaction product. The yield of the intermediate (Intermediate A) was 1424 grams and it analyzed at 1.40% nitrogen. The principal intermediate product is a succinimide represented by the formula:

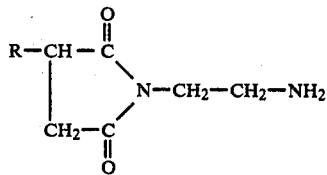

where R is a polyisobutenyl radical of about 1300 molecular weight.

The intermediate reaction product was mixed with 4-picoline in a mole ratio of one mole of succinimide to five moles 4-picoline. This mixture was heated to 110° C. and one mole equivalent of epichlorohydrin based on the succinimide was added. The resulting mixture was heated at 140° C. for 4 hours and then stripped under reduced pressure at a temperature of 100° to 110° C. to remove unreacted 4-picoline. On analysis, the resulting product (Product A) was found to contain 2.1 weight percent nitrogen and 1.49 weight percent chlorine. A key component of the reaction product is postulated to have the formula:

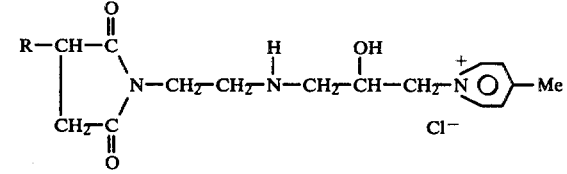

where R is polyisobutenyl of about 1300 mol. wt.

EXAMPLE II

Four hundred grams of polyisobutenyl (1300 MW) succinic anhydride (saponification number of 53), 11.3 grams of urea, 250 ml of xylene and 5 ml of water were combined, and the resulting mixture was stirred under reflux at 145° C. for 4 hours as water was removed by azeotropic distillation. The mixture was diluted with 400 grams of oil, stripped of volatiles under reduced pressure and then filtered. On analysis, this intermediate product (Intermediate B) was found to contain 0.36 weight percent nitrogen. The principal intermediate product is a succinimide postulated to be represented by the formula:

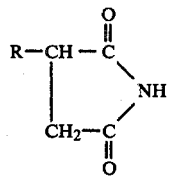

The intermediate reaction product was mixed with 4-picoline in a mole ratio of one mole of succinimide to four moles of 4-picoline. This mixture was heated to 110° C. and one and two tenths mole equivalents of epichlorohydrin based on the succinimide was added. The resulting mixture was heated at 110° C. for 8 hours and then stripped under reduced pressure at a temperature of 100° to 110° C. to remove unreacted 4-picoline. The resulting product was found to contain 0.49 weight percent nitrogen and 0.90 weight percent chlorine. A key component of the reaction product is postulated to have the formula:

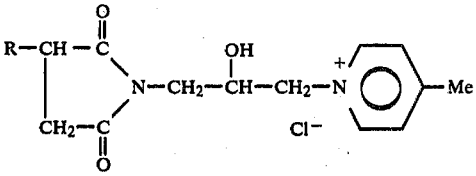

The lubricant composition of the invention comprises a major amount of a base oil, i.e., a mineral hydrocarbon oil or a synthetic oil of lubricating viscosity and effective detergent-dispersant amount of the prescribed quaternary ammonium salt. Advantageously, in the finished lubricating salt oil composition, the prescribed quaternary ammonium salt content ranges between about 0.1 and 10 percent by weight, preferably between about 0.5 and 5 weight percent. In the lubricating oil concentrates from which the finished lubricating compositions are derived via the addition of added lubricating oil, quaternary ammonium salt contents between about 10 and 60 weight percent are found. Thus, concentrations of the additive in lubricating oils and lubricating oil concentrates range from about 0.1 to 60 weight percent. The base oil in the finished lubricating composition advantageously constitutes at least about 85 weight percent and preferably between about 90 and 98 weight percent of the composition. It should be noted that the lubricating oil concentrates containing the prescribed quaternary ammonium salt will exhibit detergent/dispersancy.

Examples of the hydrocarbon base oil contemplated herein are the naphthenic base, paraffinic base and mixed base mineral oils, lubricating oils derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between about 50 and 1000, preferably between about 100 and 600, are normally employed for the lubricant compositions and concentrates thereof (SUS basis).

In the contemplated finished lubricating oil compositions other additives may be included in addition to the dispersant of the invention. The additives may be any of the suitable standard pour depressants, viscosity index improvers, oxidation, corrosion, and wear inhibitors, antifoamants, supplementary detergent-dispersants, etc. The choice of the particular additional additives to be included in the finished oils and the particular amounts thereof will depend on the use and conditions desired for the finished oil product.

The following test was employed to determine the dispersant effectiveness of the lubricant composition of the invention.

BENCH VC TEST

In the Bench VC Test, a mixture containing the test oil and a diluent are heated at an elevated temperature. After heating, the turbidity of the resultant mixture is measured. A low % turbidity (0–10) is indicative of good dispersancy while high results (20–100) are indicative of oils of increasingly poor dispersancy.

EXAMPLE III

A fully formulated SAE Grade 10W-40 lubricating oil composition containing the quaternary ammonium salt of the invention was tested for its dispersant effectiveness in the Bench VC Test in comparison to a fully formulated base oil without the amine salt dispersant and to the base oil containing the intermediate reaction product.

The base blend employed contained the following conventional additives:
0.15 weight % zinc as zinc dialkyldithiophosphate
0.23 weight % calcium as overbased calcium sulfonate
0.25 weight % alkylated diphenylamine antioxidant
11.5 weight % ethylene-propylene copolymer VI improver
0.15 weight % ethoxylated alkylphenol
0.10 weight % methacrylate pour depressant
150 ppm silicone antifoamant
mineral oil—balance (viscosity SUS at 100° F. of 120)

The quaternary ammonium salt dispersant of the invention and its precursors were added to the base blend and then tested in the Bench VC Test. The results are set forth in the table below:

TABLE I

| | BENCH VC TEST | | |
|---|---|---|---|
| Run | Lubricant Composition | Wt. %-Diluent Oil Free Basis | Turbidity |
| 1 | Base Blend (no dispersant) | — | 97.5 |
| 2 | Base Blend + Intermediate A | 3.0 | 15.0 |
| 3 | Base Blend + Intermediate B | 1.5 | 64.5 |
| 4 | Base Blend + Example 1 (Product A) | 3.0 | 6.0 |
| 5 | Base Blend + Example 2 (Product B) | 1.5 | 7.0 |

The foregoing tests demonstrate that the prescribed quaternary ammonium salts of the invention are excellent dispersants for lubricating oil compositions exhibiting an effectiveness that is superior to that of the succinimide precursors from which they were prepared.

We claim:

1. A quaternary ammonium salt composition represented by the formula:

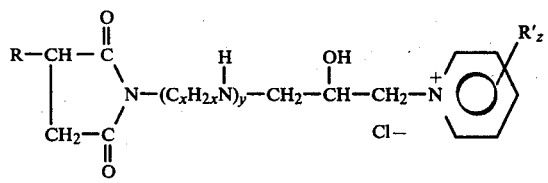

in which R is a hydrocarbyl radical having from 25 to 200 carbon atoms, x is a number from 2 to 4, y has a value from 0 to 4, R' is a hydrocarbyl radical having from 1 to 10 carbon atoms, and z is a number from 0 to 2.

2. A quaternary ammonium succinimide salt composition according to claim 1 in which R is a hydrocarbon radical having from 50 to 125 carbon atoms, x is 2 or 3, and y is 1.

3. A composition according to claim 1 in which said quaternary ammonium salt is represented by the formula:

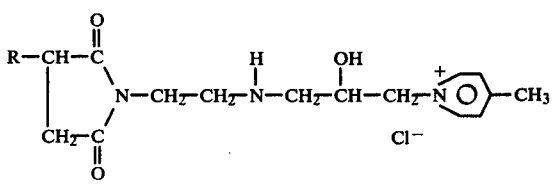

4. A composition according to claim 1 in which said quaternary ammonium salt is represented by the formula:

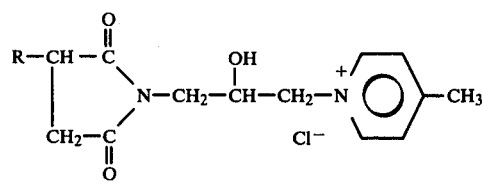

5. A composition according to claim 1 in which R is a hydrocarbyl radical having from about 70 to 100 carbon atoms.

6. A lubricant composition comprising a major portion of an oil of lubricating viscosity and a minor dispersant amount of a quaternary ammonium succinimide salt composition represented by the formula:

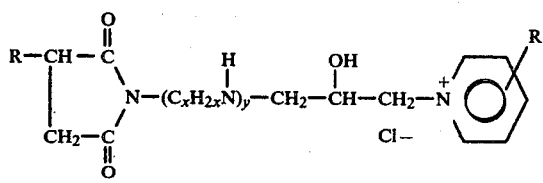

in which R is a hydrocarbyl radical having from 25 to 200 carbon atoms, x is a number from 2 to 4, and y has a value from 0 to 4, R' is a hydrocarbyl radical having from 1 to 10 carbon atoms, and z is a number from 0 to 2.

7. A lubricant composition according to claim 6 comprising a major portion of a mineral lubricating oil and a minor dispersant amount of a quaternary ammonium succinimide salt composition in which R is a hydrocarbon radical having from 50 to 125 carbon atoms, x is 2 or 3 and y is 1.

8. A lubricant composition according to claim 6 in which said quaternary ammonium salt is represented by the formula:

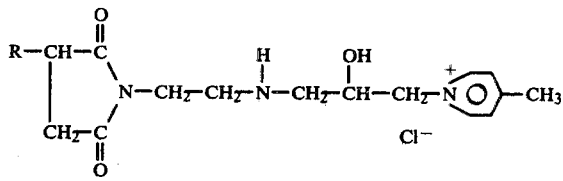

9. A lubricant composition according to claim 6 in which said quaternary ammonium salt is represented by the formula:

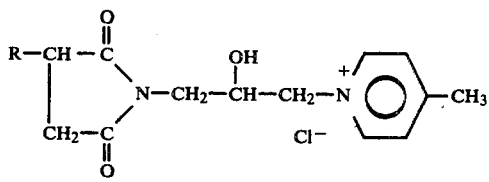

10. A lubricant composition according to claim 6 in which R is a hydrocarbyl radical having from about 70 to 100 carbon atoms.

* * * * *